(12) United States Patent
Altmann

(10) Patent No.: US 7,474,186 B2
(45) Date of Patent: Jan. 6, 2009

(54) QUANTITATIVE MEASUREMENT OF PRODUCTION AND CONSUMPTION OF GASES IN POWER TRANSFORMERS

(76) Inventor: Josef Altmann, Machova 142, Domazlice (CZ) CZ-34401

( * ) Notice: Subject to any disclaimer, the term of this patent is extended or adjusted under 35 U.S.C. 154(b) by 0 days.

(21) Appl. No.: 11/859,662

(22) Filed: Sep. 21, 2007

(65) Prior Publication Data
US 2008/0127714 A1 Jun. 5, 2008

(30) Foreign Application Priority Data
Dec. 1, 2006 (CZ) .................................. 2006-755

(51) Int. Cl.
*H01F 27/08* (2006.01)
(52) U.S. Cl. ........................................ 336/55
(58) Field of Classification Search ............ 336/55–62, 336/90–96; 324/537, 547
See application file for complete search history.

(56) References Cited

U.S. PATENT DOCUMENTS 3,531,257 A * 9/1970 Harvey et al. .................. 436/55
7,049,922 B2 * 5/2006 Sabau .......................... 336/55
2003/0164479 A1 * 9/2003 Goedde et al. .............. 252/570

* cited by examiner

*Primary Examiner*—Tuyen T. Nguyen
(74) *Attorney, Agent, or Firm*—Hovey Williams LLP

(57) ABSTRACT

A method and apparatus for quantitative DGA (Diluted Gas Analysis), providing quantitative on-line readings of gas production/consumption that directly corresponds to the extent of faults in a power transformer. This quantitative DGA method uses the oil filling of the main tank of a power transformer as a measuring capacity, enabling a physical and mathematical description of the dynamic behavior of all relevant gases in its main tank and in its conservator. A strong dynamic change of the content of a calibration gas in the oil filling of a main tank of the transformer is deliberately induced for the determination of the oil throughflow between the main tank and the conservator. Subsequently, volumetric flows of all relevant gases in a transformer are calculated from a predetermined oil throughflow, dynamic changes, and measured levels of all relevant gases that are in the main tank and the conservator.

9 Claims, 3 Drawing Sheets

QUANTITATIVE MEASUREMENT OF PRODUCTION AND CONSUMPTION OF GASES IN POWER TRANSFORMERS

BACKGROUND OF THE INVENTION

1. Field of the Invention

The invention relates to a method and apparatus for the quantitative measurement of the production or consumption of gases in power transformers and other high voltage utilities immersed in a transformer oil under normal operational conditions.

2. Description of Prior Art

The existing solution for the identification and diagnosis of faults in power transformers related to their gas production or consumption is based on the so-called DGA method (Diluted Gas Analysis method). This method utilizes the fact that gases, which are either generated directly in the transformer or transported into it's oil filling from the surrounding air, are under standard conditions fully dissolved in the oil filling. To detect whether the given gas is present in the transformer or not and in what concentration, a sample of oil from the oil filling of the given transformer is taken. Gases are then extracted from the oil under vacuum and fed into a DGA analyzer. The analyzer output gives a relatively high accuracy reading of the content of selected gases contained in the sampled oil.

This first step is followed by a diagnostic procedure, which identifies gas sources and the corresponding faults of a transformer. From the absolute values of measured gases and from their proportional representation, the procedure determines the extent of specific faults in the transformer.

However, the practice shows that such a diagnostic method, especially the evaluation of the intensity of the aging of cellulose materials in the transformer, can be highly misleading. The basic and ultimate deficiency of the current DGA diagnostic of transformer faults arises from an improper description of the transportation of gases in the transformer.

Any transformer generally represents an open system where gases, under standard operational conditions (produced/consumed), are diluted in the oil filling of the main tank and transported out of or into the main tank by the oil. The oil steadily flows between the main tank and the conservator (from where gases more or less freely escape into/ infiltrate from the atmosphere).

The absolute content of a specific gas in the oil filling of a transformer depends therefore not only on the extent of a specific fault (which produces/consumes the specific gas), but also depends on the intensity of the transport of the specific gas from or into the oil filling of the main tank of a transformer.

The apparent and fundamental deficiency of the current DGA diagnostics is that this method pre-supposes that the transport of gases out of or into a transformer is always more or less constant and does not play any important role there.

This presumption is wrong, because the throughflow of the oil between the main tank and the conservator strongly varies and, in the same way, varies the amount of gases, which escape from and infiltrate into the transformer.

A high or low concentration of a specific gas in the oil filling of the main tank of a transformer is therefore not only caused by either a high or low production or consumption of a specific gas in the transformer. It may also be due to the transport conditions of this gas in or out of the oil filling of the main tank.

This problem can be illustrated by a simple hydraulic analogy. The actual level of the water in a tank depends not only on the inflow but also on the outflow of the water from a tank. With the increase of the water level in this tank, it could be pre-suppose that this increase was induced by the increase of the inflow. This increase however could also be induced by the decrease of the outflow of water, so by only looking at the actual level of the water in the tank, it is not possible to find out what actually caused the change.

Moreover, under the quasi-equilibrium condition (the water level in the tank remains quasi-constant), it is simply impossible to determine the inflow/outflow of the water into/ from this tank by a reading of the water level in the tank only (how many litres of water per second flow through the tank?).

These facts illustrate the basic problem of the present DGA diagnostic, because a simple reading of the absolute content of gases in the oil filling of the transformer main tank alone cannot provide us with relevant information about gas sources (faults) or gas sinks (e.g. consumption of O2) in this system.

Theoretically, it is possible to get a very high reading of the specific gas (high level of water in the tank) by the low production of a given gas from a corresponding internal fault (very low inflow of the water in the tank) if a very low escape (very low outflow) of this gas (water) is present from the main tank. On the other hand, the result could be a very low reading of the same gas produced by a relatively big fault if there exists a strong throughflow of the oil between the main tank and the conservator that intensively transports the gas out of the main tank into the surrounding air).

Because the transformer oil always serves as a "porter" of diluted gases, only precise DGA diagnostics of any faults is impossible without the equally precise determination of the oil throughflow between the main tank and the conservator.

The problem is that this direct reading of the oil throughflow is, under standard operational conditions of a transformer, very difficult or impractical. The oil throughflow is here generally controlled by several different variables, namely:

the temperature of the transformer (the change of oil temperature induces the strong dilatation of the oil filling in the main tank), the temperature difference between the oil filling and the surrounding air, and typical constants for given transformers corresponding to its specific design for the diameter, length and slope of the tube connecting the upper part of the main tank and the bottom part of the conservator.

The usual conception that the oil throughflow between the main tank and the conservator is induced only by the dilatation of the oil filling of the main tank is wrong and misleading. Under standard operational conditions there always exists the permanent throughflow of oil between both tanks induced by the thermosiphon effect and its intensity is predominantly affecting the temperature difference between the main tank and conservator.

Any change of the transformer temperature, load, or air temperature thus inevitably and immediately changes the oil throughflow between the transformer tank and the conservator and subsequently the concentration of gases in the oil filling of the transformer main tank, though it's own production/consumption of gases may not change there.

In principle, a relatively negligible fault in the transformer, under given conditions, may be evaluated as a big fault and vice-versa.

Moreover, as already mentioned above, the current DGA represents only so-called qualitative diagnostics. By reading the specific gas in the main tank of a transformer, it can be determined (qualitatively and exactly) that there must exist a specific fault, but because the flow of corresponding gas cannot be measured, the extent of a specific fault cannot be quantified.

The present DGA, based on the quasi-equilibrium saturation of the oil filling of the main tank of a transformer, therefore excludes any standard measuring method of the gas production or consumption in a transformer in the technically required measuring units of $m^3/s$ or kg/s.

The current DGA diagnostic then inevitably produces a wide range of more or less anomalous or even wrong conclusions of the status of the monitored transformer.

Generally, the current DGA diagnostic method has at least three fundamental drawbacks:

It does not respect the physical reality of the measured system.

It works only under quasi-equilibrium conditions and is therefore not able to quantify faults in a transformer.

It is not able to discriminate whether the measured growth or decline of the level of the specific gas is caused by either the growth or reduction of the fault, or by the change of boundary conditions (i.e. by the change of the transformer temperature, load etc.).

SUMMARY OF THE INVENTION

The present invention is a method and apparatus for quantitative DGA using the oil filling (the volume of which can be easily and precisely determined) of the main tank of a transformer as a measuring capacity enabling a precise physical and mathematical description of the dynamic behaviour of all relevant gases in its main tank and in its conservator.

At first, a strong dynamic change of the content of a so-called calibration gas (not produced or consumed in a transformer) in the oil filling of a main tank of a transformer is deliberately induced for the determination of the oil throughflow between the main tank and the conservator. Subsequently, volumetric flows of all relevant gases in a transformer are calculated from a predetermined oil throughflow, dynamic changes, and measured levels of all relevant gases that are in the main tank and the conservator.

More specifically, the method of the present invention is generally based on on-line, time-related, DGA readings and a dynamic approach to the diagnostics of faults of power transformers.

The method of quantitative measurement is built on the following presumptions:

The capacity of the oil filling of the main tank can be precisely determined and used as a measuring capacity enabling a precise physical and mathematical description of the dynamic behaviour of all gases in the main tank.

The oil throughflow between the conservator and the main tank is measured by the utilization of the deliberate dynamic change of the content of a so-called calibration gas (which is not produced or consumed in a transformer) in the main tank or the conservator:

the content of the calibration gas in the oil filling of the tank is purposely changed (lowered or increased) to reach strong non-equilibrium starting conditions subsequently the following growth (or decline) of the calibration gas content is read on-line not only in the oil filling of the transformer tank but in the conservator as well.

The flows of all gases into/from the transformer tank are then defined by:

measuring of oil flow rate between the transformer tank and the conservator, measuring the concentration of all relevant gases in the transformer tank and in the conservator, and evaluating actual concentration gradients of all relevant gases in the main tank.

To achieve a sufficient dynamic response in the calibration gas concentration in the oil filling of the main tank and thus the requested measurement accuracy, it is necessary for either:

vacuum treatment of oil filling of the main tank (In vacuum treatment of oil filling of the main tank, the oil filling is degassed at first, then the content of the calibration gas (and all other gases, as well) in the oil is substantially reduced to get, and after the disconnection of the vacuum gas separator the sufficient dynamic response in a measured resaturation of the oil filing of the main tank by the calibration gas (usually by nitrogen from the air surroundings), or saturation of the oil filling of the conservator by a special calibration gas from an external source (not existing in the transformer but inert). The fast growth of the content of this gas in the conservator then induces the required dynamic response of the content of this gas in the oil filling of the main tank.

Nevertheless, the calibration gas (K) must always itself behave in the transformer as an inert gas (may not be produced or consumed there either). The dynamics of its concentration in the main tank (with volume Vn), can be described by a differential equation:

$$Vn \cdot dCK,n/dt = vo \cdot (CK,kon - CK,n) \tag{1}$$

where:

Vn . . . oil volume of main tank dCK,n/dt . . . saturation gradient of calibration gas (K) in oil filling of main tank vo . . . volumetric oil flow between conservator and main tank CK,kon . . . content of calibration gas in conservator (kon) oil filling CK,n . . . content of calibration gas in main tank (n) oil filling dt . . . time increment This simplified mathematical model (for simplicity, the temperature of the transformer is assumed here to be approximately constant) is the real diagnostic procedure and the change of the temperature is of course taken into account. This enables calculation of the first and very important value in the system—the virtual throughflow of the oil between the main tank and the conservator:

$$vo = Vn \cdot (dCK,n/dt)/(CK,kon - CK,n) \tag{2}$$

The virtual oil flow (vo) will cause, for the continuously measured level of the calibration gas in the main tank (CK,n) and in the conservator (CK,kon), the ascertained gradient of the calibration gas (dCK,n/dt) in the main tank. The basic analytical approach based on the evaluation of the on-line measured saturation curve of the calibration gas in the main tank is shown at FIG. 1.

Subsequent evaluation of the production of the gas X by a fault in the main tank is easy, because each single gas X behaves in the oil filling of the transformer tank as if it was there alone, thus the dynamics of the gas concentration can be expressed by another differential equation:

$$Vn \cdot dCX,n/dt = vo \cdot (CX,kon - CX,n) + vX \tag{3}$$

Because the contents CX,kon and CX,n are continuously measured as well, the gradient of the content of the gas X can be evaluated in the same way as by the calibration gas, and because the volumetric flow of the oil between the main tank and the conservator is known, the volumetric flow vX of fault gas X can be directly calculated as:

$$vX = Vn \cdot dCX,n/dt - vo \cdot (CX,kon - CX,n) \quad (4)$$

where:

vX ... volumetric flow of the gas X produced by the fault X in the main tank dCX,n/dt ... gradient of the gas concentration X in the main tank vo ... known volumetric flow of the oil between the conservator and the main tank CX,kon ... content of the gas X measured in oil filling of the conservator CX,n ... content of the gas X measured in oil filling of the main tank In the other words, the volumetric flow of gases X (vx) from the fault X in the main tank of a transformer can be easily determined by means of measured, time-related change (dCX,n/dt) of the content of the gas X in the known oil volume (Vn) of its main tank, corrected by the inflow (vo·CX,kon) of the gas X from its conservator and the outflow (vo·CX,n) of this gas from its main tank.

In the same way, it is possible to calculate the consumption of the gas (O2) in the main tank:

$$Vn \cdot dCO2,n/dt = vo \cdot (CO2,kon - CO2,n) - vO2 \quad (5)$$

Because the oil volumetric flow vo and both O2-levels in the main tank and the conservator and the O2-gradient in the main tank are known, the volumetric flow of the oxygen consumed by aging processes in the main tank can be easily evaluated. It can be expressed as:

$$vO2 = vo \cdot (CO2,kon - CO2,n) - Vn \, dCO2,n/dt \quad (6)$$

VO2 ... volumetric flow of the oxygen consumed in the main tank dCO2,n/dt ... gradient of the oxygen content in the main tank vo ... volumetric flow of oil between the conservator and the main tank CO2,kon ... oxygen content measured in oil filling of the conservator CO2,n ... oxygen content measured in oil filling of the main tank The advantage of this quantitative measurement of the production or consumption of gases in a transformer, based on this invention is, in particular, the fact that such a measurement method provides relevant quantitative on-line readings of gas production/consumption that directly corresponds to the extent of faults in the transformer.

Another advantage of this measurement method is the possibility to check and recalibrate historical data acquired by a standard DGA method to eliminate or rectify wrong diagnostic conclusions.

Another important benefit of such a method is the fact that this diagnostic procedure can be carried out any time, on any transformer without any adaptations, under normal operational conditions, and gives a real on-line picture of the problems of any given transformer.

DETAILED DESCRIPTION OF THE INVENTION

Figure 1:
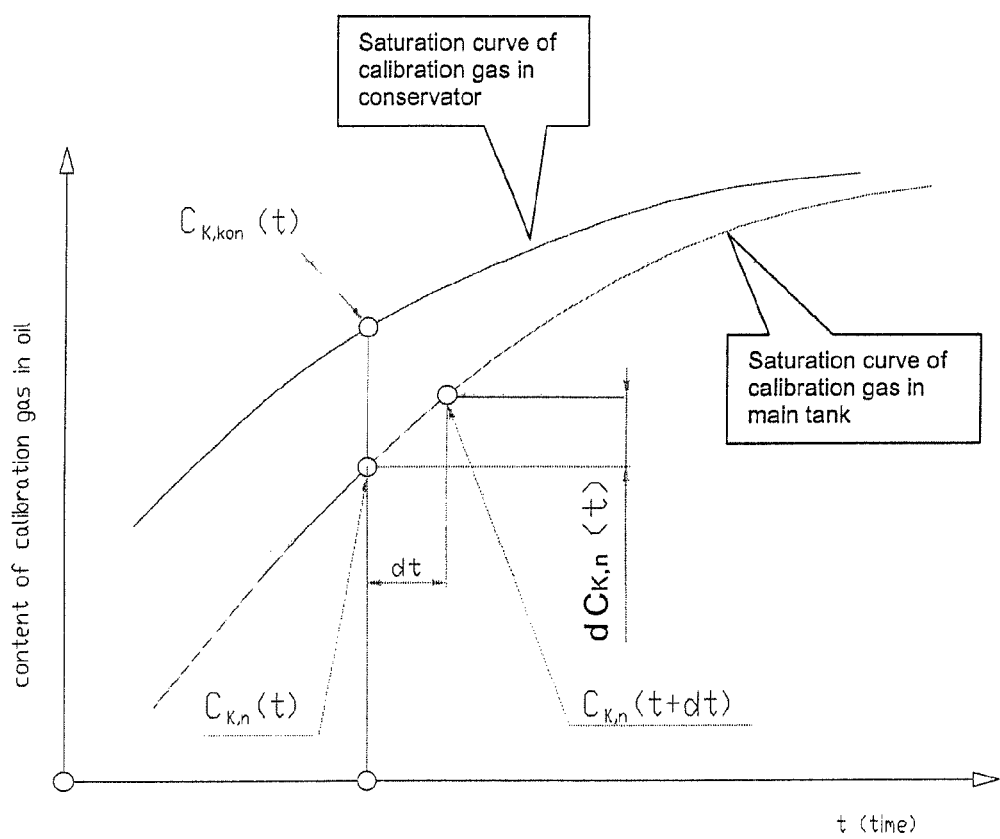
FIG. 1 shows the time-related reading of the calibration gas in the main tank and the conservator of a transformer and the evaluation of a gradient of the calibration gas in the main tank.
Figure 2:
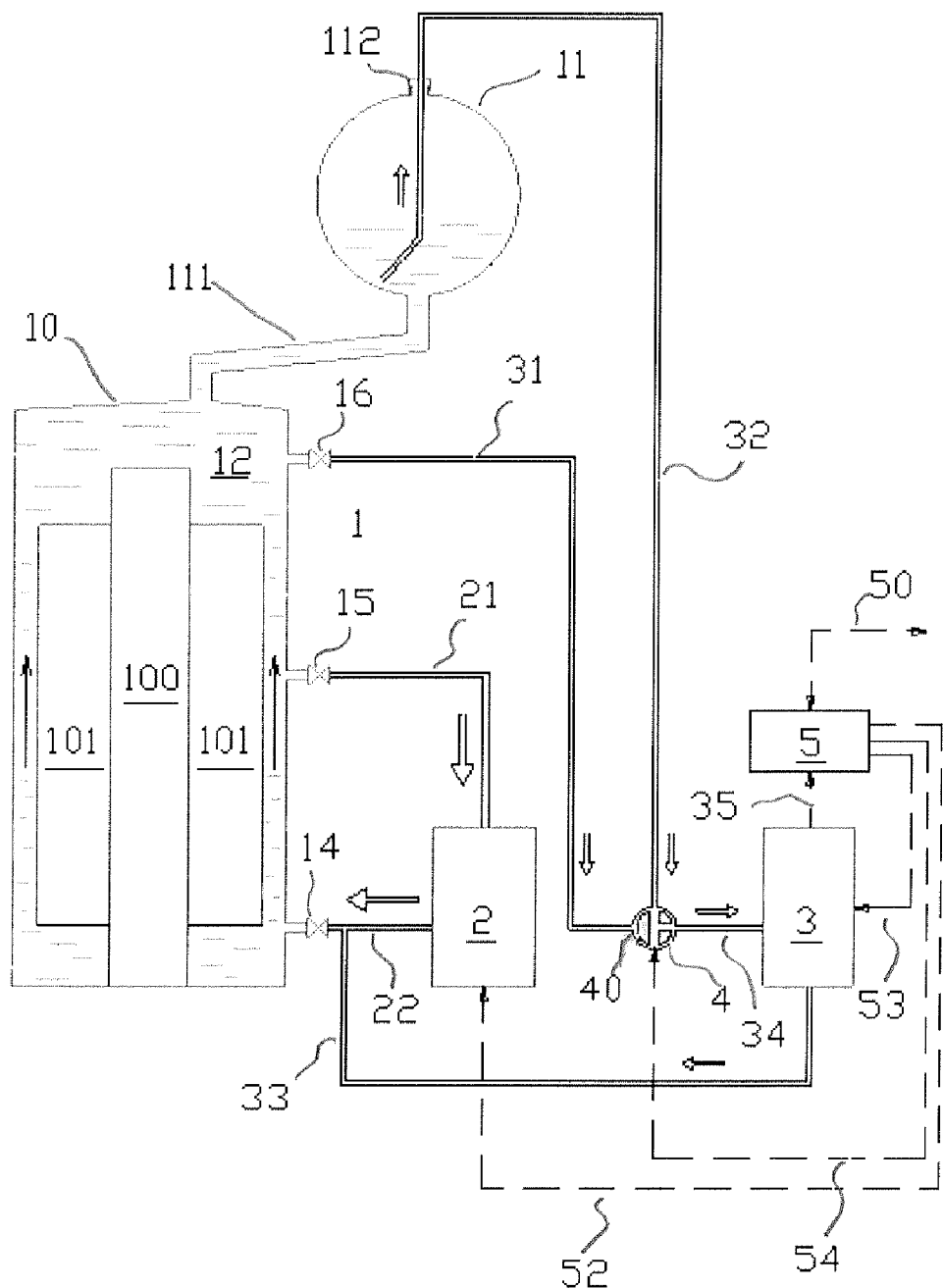
FIG. 2 schematically shows the device for the quantitative measurement with the invention where the dynamic response of the content of a calibration gas in the main tank is achieved by the vacuum treatment of the oil in the main tank.

An embodiment of the invention is shown in FIG. 2, and primarily includes the transformer 1, consisting of the main tank 10, where the magnetic circuit 100 and the winding 101 is situated. The conservator 11 is located above the main tank 10 and is connected by the connecting tube 111. In turn, from the main tank 10, the degassing device 2, the DGA analyzer 3, the hydraulic reversing switch 4 and the PCD (Process Control Device) 5 are linked.

The lower part of the main tank 10 is hydraulically connected by means of the bottom sampling cock 14 and the bottom tube 22 to the degassing device 2. The middle part of the main tank is hydraulically connected by the middle sampling cock 15 and the middle tube 21 to the degassing device 2. The reversing switch 4 is connected by the pipe 31 to the upper sampling cock 16 at the upper part of the main tank 10. The upper pipe 32 goes through the plug 112 located in the upper part of the conservator 11 and leads to the bottom part of the sphere. The DGA analyzer 3 is, through the sleeve 34, connected to the reversing switch 4 and also connected by the drainage tube 33 to the bottom tube 22.

The electrical circuits of the first practical aspect of the invention include measuring and control lines which connect the PCD 5 with the DGA analyzer 3, reversing switch 4 and the degassing device 2. The first control line 53 connects the PCD 5 with the DGA analyzer 3 and the second control line 54 connects the PCD 5 with the reversing switch 4. The third control line connects the PCD 5 with the degassing device 2. The PCD 5 is also connected by the communication line 50 to a remote PC (not shown).

A second embodiment of the invention is shown in FIG. 3, and once again includes the transformer 1, the conservator 11, the DGA analyzer 3, the hydraulic reversing switch 4, the calibration gas flask 6, and the PCD (Process Control Device) 5.

In this case, the lower part of the main tank 10 is by means of the bottom sampling cock 14 hydraulically connected by the drainage pipe 33 to the DGA analyzer 3. The upper part of the main tank is by means of the upper sampling cock 16 hydraulically connected by the pipe 31 to the hydraulic reversing switch 4. This switch is also by means of the upper pipe 32 connected to the bottom part of the conservator 11 and by the sleeve 34 with the DGA analyzer 3. The conservator is connected by the gas pipe 61 to the servovalve 60 located at the calibration gas flask 6.

Figure 3:
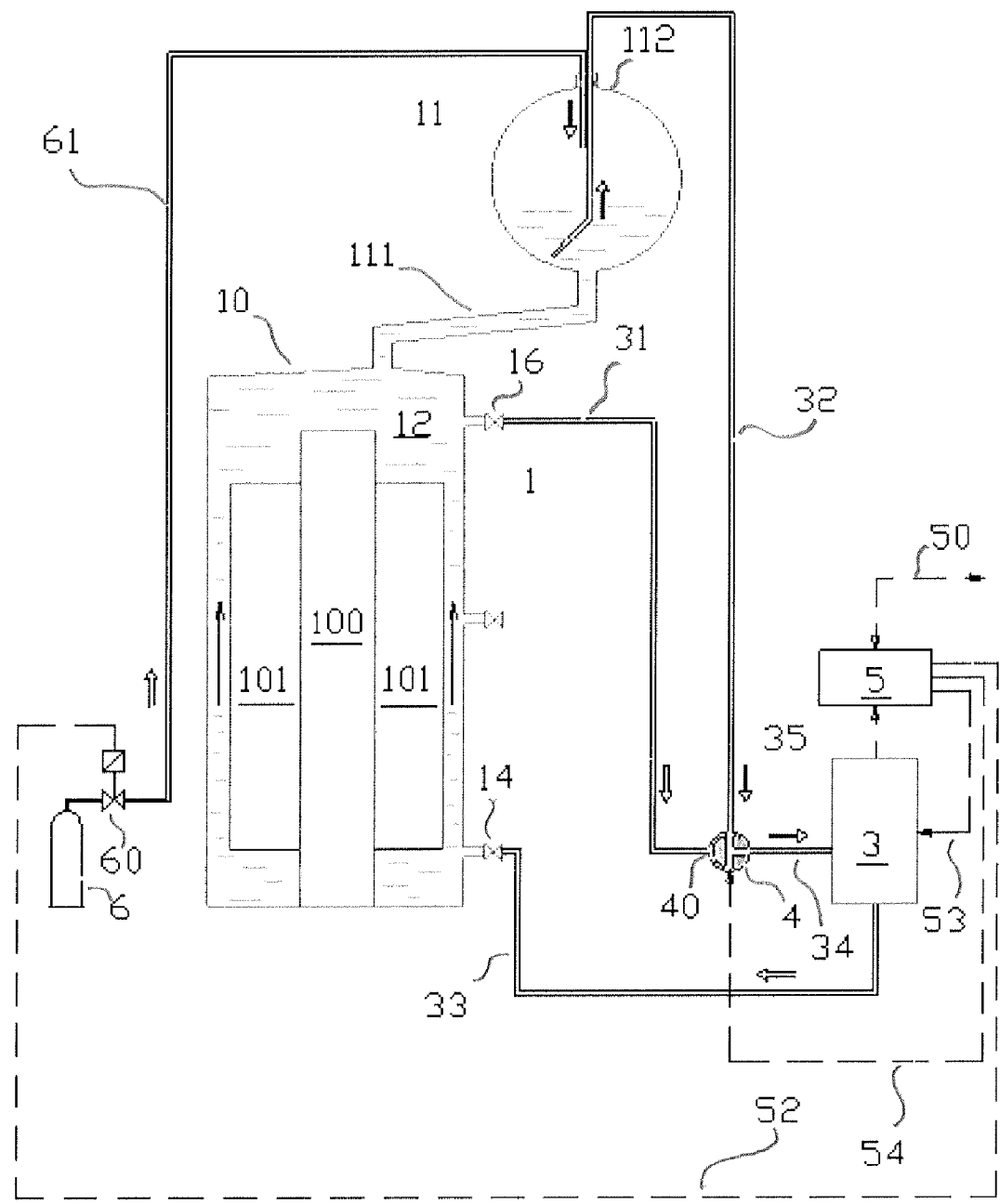
FIG. 3 schematically shows the device for the quantitative measurement with the invention, where the dynamical response of the content of a calibration gas in the main tank is achieved by saturation of the oil filling of the conservator by the supply of the calibration gas from an external source

The electrical circuits of the embodiment of the invention shown on FIG. 3 include measuring and control lines which connect the PCD 5 with the DGA analyzer 3, the reversing switch 4 and the servo valve 60 of the calibration gas flask 6. The first control line 53 connects the PCD 5 with DGA analyzer 3. The second control line 54 connects the PCD 5 with the reversing switch 4. The third control line connects the PCD 5 with the servovalve 60 located on the flask 6. The PCD 5 is also connected by the measuring line 35 with the DGA analyzer 3 and by the communication line 50 with a remote PC (not shown).

The operation of the first embodiment of the invention (FIG. 2) works in two basic steps. At first, the oil filling 12 of the main tank 10 is degassed by the degassing device 2 and the content of the "natural" calibration gas (nitrogen) in the oil is, in this way, strongly reduced. In the second step the degassing device 2 is shut down and the oil filling 12 of the main tank 10 is re-saturated by the nitrogen from the surrounding air diluted in the oil inflowing from the conservator 11.

The entire diagnostic procedure, under normal conditions, runs fully automatically. Only the bottom sampling cock 14, middle sampling cock 15, and upper sampling cock 16 have to be manually opened before the start of the diagnostic procedure.

The PCD 5 via the third control line 52 starts up the degassing device 2 and simultaneously switches the three-way actuator 40 of the reversing switch 4 into position where the oil from the main tank 10 flows through the upper sampling cocks 16, the pipe 31, the three-way actuator 40 of the reversing switch 4 and the sleeve 34 directly into the DGA analyzer 3. The DGA analyzer continuously measures the actual content of the calibration gas in the oil and the oil is then discharged by the discharging pipe 33 and the bottom pipe 22 back into the oil filling 12 of the main tank 10.

The degassing device 2 gradually decreases the content of the calibration gas in the oil filling 12 of the main tank 10 and when the content of the calibration gas sinks under a pre-defined level, the PCD 5 switches the degassing device 2 off and it's own diagnostic procedure begins.

Simultaneously, in the pre-defined time interval, the PCD 5 signal activated by the second control line 54 changes the position of the three-way actuator 40 of the reversing switch 4 back and forth and the DGA analyzer 3 reads reversely the contents of all relevant gases in the oil inflow via the pipe 31 from the main tank 10 and via the upper pipe 32 from the conservator 11. This is via the pipe 31 and from the conservator 11 via the upper pipe 32. The PCD 5 then calculates the throughflow of the oil between the main tank 10 and the conservator 11 and subsequently the production of fault gases and e.g. consumption of the O2 (measured in universally accepted units).

The diagnostic procedure is terminated if the time-gradient of the calibration gas and/or the difference between contents of calibration gas in the main tank 10 and the conservator 11 becomes too low. As a result, not only the precision of the reading, but also the precision of the evaluation of the oil throughflow between the main tank and the conservator decreases under a pre-defined limit.

The attainable time span of the first on-line DGA diagnostic procedure integral to the invention under standard conditions exceeds several months (for example, two or more months) and enables therefore a very good monitoring of all relevant faults and their sensitivity to changes of actual parameters of the transformer.

The operation of the second embodiment of the invention (FIG. 3) works with two basic steps:
with the saturation stage, where the content of the calibration gas in the main tank, due to the external supply, increases, and
with the de-saturation stage, where the calibration gas freely escapes from a transformer into the surrounding air.

The PCD 5 opens the servovalve 60 via the third control line 52 at the pressurized calibration gas storage flask 6 and the calibration gas flows through the gas tube 61 into the conservator 11 and diffuses into its oil filling. It is subsequently transported by the oil into the main tank 10.

The DGA analyzer 3 continuously reads increasing content of the calibration gas in the oil filling 12 of the main tank 10, and if its time-gradient exceeds a pre-defined limit, it's own diagnostic procedure begins (the precision of the measurements and evaluation are taken for granted).

The PCD 5, in the pre-defined time interval, changes, via the signal of the second control line 54, the position of the three-way actuator 40 of the reversing switch 4 back and forth. The DGA analyzer 3 reads in reverse the contents of all relevant gases in the oil inflowing from the main tank 10 via pipe 31 and from the conservator 11 via upper pipe 32. The PCD 5 then calculates the actual throughflow of the oil between the main tank 10 and the conservator 11 and subsequently the production of fault gases and e.g. consumption of the O2 (measured in universally accepted units, e.g. ml/day).

The attainable time-interval of on-line DGA diagnostic procedure under standard conditions is, in this case, virtually unlimited and depends, in principle only, on the storage capacity of the flask 6.

If, during the saturation stage of the oil filling of a transformer, the gradient of the calibration gas in the oil filling of its main tank becomes lower than a pre-defined limit (the gas level in the oil filling gets near the saturation level) the servovalve 60 is closed, stopping the inflow of the calibration gas in the conservator 11. The measuring system then changes into the second, de-saturation stage where the calibration gas freely escapes from the transformer 1 in the surrounding air. The content of the calibration gas in the oil filling 12 of the main tank 10 adequately decreases and this dynamic process can be utilized again for the measuring of gas flows in the now measured system in the same way as before.

If the gradient of the calibration gas in the oil filling 12 of the main tank 10 sinks under a pre-defined limit, the servovalve 60 on the flask 6 opens again and the measuring process starts from the beginning.

In this way the second on-line DGA diagnostic procedure integral to the invention enables, in principle, an unlimited on-line monitoring of pertinent faults and their sensitivity to changes of actual parameters of a transformer (only the calibration gas flask must be changed regularly).

Although the invention has been described with reference to the preferred embodiments illustrated in the attached drawings, it is noted that equivalents may be employed and substitutions made herein without departing from the scope of the invention as recited in the claims.

Having thus described a preferred embodiment of the invention, what is claimed as new and desired to be protected by Letters Patent includes the following:

1. A method of quantitative measurement of production or consumption of gases in a power transformer, comprising the steps of:
providing a power transformer including:
a main tank including a magnetic circuit, a winding, a bottom sampling cock, a middle sampling cock and an upper sampling cock;
a conservator having an upper part, said upper part including a plug;
a connecting tube fluidically connecting the upper part of the conservator to the main tank;
providing a quantity of oil in the main tank;
providing a calibration gas in the main tank;
determining the internal volume of the oil in the main tank to provide a measuring capacity;
determining a flow of oil flow in the connecting tube between the conservator and the main tank; and
measuring the deliberate dynamic change of the content of the calibration gas in the main tank.

2. A method of quantitative measurement of production or consumption of gases as set forth in claim 1, including the steps of actively changing the amount of the calibration gas in the main tank by a measuring device coupled to the transformer to produce non-equilibrium starting conditions, measuring the amount of the calibration gas in the oil in the main tank and the conservator, and calculating the flow of oil between the main tank and the conservator.

3. A method of quantitative measurement of production or consumption of gases as set forth in claim 2, including the step of continuously measuring the amount of all gases in the main tank and in the conservator, and thereafter calculating the production or consumption of gases in the main tank according to the flow of oil between the main tank and the conservator.

4. A power transformer comprising:
   a main tank including a magnetic circuit, a winding, a bottom sampling cock, a middle sampling cock and an upper sampling cock;
   a conservator having an upper part;
   a connecting tube fluidically connecting the upper part of the conservator to the main tank;
   a device for determining the quantitative measurement or production of gases in the transformer comprising:
      a degassing device;
      a diluted gas analysis (DGA) analyzer;
      a reversing switch having a three way actuator;
      a first pipe fluidically connecting said reversing switch with said upper sampling cock to said main tank;
      a process control device (PCD);
      a middle tube fluidically connecting said degassing device to said main tank via said middle sampling cock;
      a bottom tube fluidically connecting said degassing device to said main tank via said bottom sampling cock;
      a second pipe connecting said conservator to said reversing switch;
      a conduit fluidically connecting said bottom tube to said DGA analyzer;
      a first control line operatively connecting said PCD to said DGA analyzer;
      a second control line operatively connecting said PCD to said reversing switch; and
      a third control line operatively connecting said PCD to said degassing device.

5. A power transformer as set forth in claim 4, said upper part of said conservator including a plug, wherein said second pipe is connected to said plug for fluidically connecting said conservator to said reversing switch.

6. A power transformer as set forth in claim 4, further including a connecting line adapted for electronically coupling said PCD to a computer.

7. A power transformer comprising:
   a main tank including a magnetic circuit, a winding, a bottom sampling cock, a middle sampling cock and an upper sampling cock;
   a conservator having an upper part;
   a connecting tube fluidically connecting the upper part of the conservator to the main tank;
   a device for determining the quantitative measurement or production of gases in the transformer comprising:
      a flask containing a quantity of calibration gas;
      a gas tube fluidically connecting said flask to said conservator;
      a valve connected to said gas tube fluidically intermediate said flask and said conservator;
      a diluted gas analysis (DGA) analyzer;
      a reversing switch having a three way actuator;
      a first pipe fluidically connecting said reversing switch with said upper sampling cock to said main tank;
      a process control device (PCD);
      a bottom tube fluidically connecting said DGA analyzer to said main tank via said bottom sampling cock;
      a second pipe connecting said conservator to said reversing switch;
      a first control line operatively connecting said PCD to said DGA analyzer;
      a second control line operatively connecting said PCD to said reversing switch; and
      a third control line operatively connecting said PCD to said valve for controlling the flow of gas through said gas tube.

8. A power transformer as set forth in claim 7, said upper part of said conservator including a plug, and wherein said second pipe is connected to said plug for fluidically connecting said conservator to said reversing switch.

9. A power transformer as set forth in claim 7, further including a connecting line adapted for electronically coupling said PCD to a computer.

* * * * *